United States Patent
Hauser et al.

(10) Patent No.: US 11,872,238 B2
(45) Date of Patent: Jan. 16, 2024

(54) NUTRITIONAL COMPOSITION FOR USE TO ENHANCE ATTENTION AND/OR REDUCE IMPULSIVITY

(71) Applicant: SOCIETE DES PRODUITS NESTLE S.A., Vevey (CH)

(72) Inventors: Jonas Hauser, Lausanne (CH); Simone Macri, Rome (IT)

(73) Assignee: Societe des Produits Nestle S.A., Vevey (CH)

(*) Notice: Subject to any disclaimer, the term of this patent is extended or adjusted under 35 U.S.C. 154(b) by 0 days.

(21) Appl. No.: 16/615,897

(22) PCT Filed: May 22, 2018

(86) PCT No.: PCT/EP2018/063294
§ 371 (c)(1),
(2) Date: Nov. 22, 2019

(87) PCT Pub. No.: WO2018/215406
PCT Pub. Date: Nov. 29, 2018

(65) Prior Publication Data
US 2020/0121702 A1 Apr. 23, 2020

(30) Foreign Application Priority Data
May 24, 2017 (EP) .................................. 17172900

(51) Int. Cl.
*A61K 31/702* (2006.01)
*A61P 25/00* (2006.01)
*A61K 9/00* (2006.01)

(52) U.S. Cl.
CPC .......... *A61K 31/702* (2013.01); *A61K 9/0095* (2013.01); *A61P 25/00* (2018.01)

(58) Field of Classification Search
CPC ...... A61K 31/702; A61K 9/0095; A61P 25/00
USPC ......................................................... 514/61
See application file for complete search history.

(56) References Cited

U.S. PATENT DOCUMENTS

| | | |
|---|---|---|
| 2003/0005477 A1 | 1/2003 | Leviten |
| 2007/0142319 A1 | 6/2007 | Marth et al. |
| 2011/0206649 A1 | 8/2011 | Bergonzelli Degonda et al. |
| 2012/0171166 A1 | 7/2012 | Chow et al. |
| 2014/0242050 A1 | 8/2014 | Bergonzelli Degonda et al. |
| 2014/0271562 A1 | 9/2014 | Garcia-Rodenas et al. |
| 2015/0231159 A1 | 8/2015 | Hernandez et al. |
| 2015/0320778 A1 | 11/2015 | Chow et al. |

FOREIGN PATENT DOCUMENTS

| | | | |
|---|---|---|---|
| CN | 102458150 A | 5/2012 | |
| EP | 2454948 A1 * | 5/2012 | ............ A23L 1/296 |
| WO | 2016145628 A1 | 9/2016 | |
| WO | 2016146789 | 9/2016 | |

OTHER PUBLICATIONS

Tucha et al.( J Neural Transm (2017) 124 (Suppl 1):S39-S53).*
Allen et al. (Frontiers in Bioscience 6, d105-119, Jan. 1, 2001).*
Wang et al. "Dietary sialic acid supplementation improves learning and memory in piglets" Am J Clin Nutr, 2007, vol. 85, pp. 561-569.
Grosswald, Sarina J. "Is ADHD a Stress-Related Disorder? Why Meditation Can Help" Attention Deficit Hyperactivity Disorder in Children and Adolescents, Jun. 27, 2013, InTech, 22 pages.
Jacobi et al. "Dietary Isomers of Sialyllactose Increase Ganglioside Sialic Acid Concentrations in the Corpus Callosum and Cerebellum and Modulate the Colonic Microbiota of Formula-Fed Piglets" The Journal of Nutrition, 2016, vol. 146, pp. 200-208.
Wang, Bing "Sialic Acid Is an Essential Nutrient for Brain Development and Cognition" Annual Review of Nutrition, 2009, vol. 29, pp. 177-222.
Chinese Office Action dated Oct. 12, 2023 for App. No. 20188028293.0 (8 pages).

* cited by examiner

*Primary Examiner* — Layla D Berry
(74) *Attorney, Agent, or Firm* — K&L Gates LLP

(57) ABSTRACT

Use of a sialyllactose, or a nutritional composition comprising a sialyllactose, to enhance attention and/or to decrease impulsivity in a subject.

8 Claims, 4 Drawing Sheets

NUTRITIONAL COMPOSITION FOR USE TO ENHANCE ATTENTION AND/OR REDUCE IMPULSIVITY

CROSS REFERENCE TO RELATED APPLICATIONS

The present application is a National Stage of International Application No. PCT/EP2018/063294, filed on May 22, 2018, which claims priority to European Patent Application No. 17172900.7, filed on May 24, 2017, the entire contents of which are being incorporated herein by reference The present invention relates to the use of a sialyllactose, or a composition comprising a sialyllactose, to enhance attention and/or to reduce impulsivity in a subject. The invention further relates to a sialyllactose, or a composition comprising a sialyllactose, for use in the prevention or treatment of reduced attention and/or excess impulsivity in a subject.

BACKGROUND OF THE INVENTION

Attention is the ability to focus on information or stimuli, it is a cognitive function that is essential for day to day functioning and one that is fundamental to learning. In fact, attention is believed to be so fundamental to learning that it is considered by many as a marker of intelligence and a key determinant of IQ and academic achievement. Another determinant of IQ and academic achievement may be impulsivity, a behaviour that may be described as acting with little or no forethought and consideration of the consequences. Given the associations between attention, impulsivity, intelligence, and academic achievement, there is a desire to find ways to enhance attention and to reduce impulsivity.

In addition to finding ways to enhance attention and to reduce impulsivity, there is also a need to find ways to treat and/or prevent reduced attention and/or excess impulsivity. Reduced attention and or excess impulsivity can impede learning and adversely affect intelligence and academic achievement. Depending on the severity, reduced attention and excess impulsivity can even negatively affect day to day functioning.

Reductions in attention and excess impulsivity may be linked to a variety of cognitive conditions including Attention Deficiency Hyperactivity Disorder (ADHD), Alzheimer's disease, and vascular dementia; it is also known that attention can decline with aging. Accordingly, there may be a particular need to prevent or treat reduced attention and/or excess impulsivity in these patient groups.

Surprisingly the inventors have now found that consumption of a sialyllactose, in particular 6'-sialyllactose (6'-SL), may enhance attention and/or to reduce impulsivity in a subject. This finding stems from a study in mice, the results of which indicated that mouse pups receiving milk absent of a sialyllactose, in particular 6'-sialyllactose (6'-SL), showed, when evaluated as adults, decreased attention, and increased impulsivity in comparison to mouse pups receiving milk comprising a sialyllactose, in particular 6'-sialyllactose (hereinafter 6'-SL). This effects were observed on a background of no changes in term of neurodevelopment evaluated by the onset and strength of reflexes using the Fox scale.

SUMMARY OF THE INVENTION

The invention is set out in the claims and in the detailed description included herein.

The present invention provides the use of a sialyllactose or a nutritional composition comprising a sialyllactose to enhance attention and/or to decrease impulsivity in a subject.

The present invention also provides a sialyllactose or a nutritional composition comprising a sialyllactose for use in the treatment and/or prevention of reduced attention and/or excess impulsivity in a subject.

The sialyllactose may be selected from the group consisting of 3'-sialyllactose (3'-SL), 6'-sialyllactose (6'-SL), and a combination thereof. It may be particularly beneficial if the sialyllactose is 6'-sialyllactose.

Attention may be sustained attention, divided attention, and a combination of any of the foregoing. A sialyllactose, or nutritional composition comprising a sialyllactose, may be particularly effective at enhancing sustained attention, or at treating and/or preventing reduced sustained attention.

The subject may be a mammal and for example may be a human or companion animal. The sialyllactose, or nutritional composition comprising a sialyllactose, may be particularly suited for, or particularly effective in, a human infant.

Administration of a sialyllactose, or nutritional composition comprising a sialyllactose, to a human infant may be in-utero or via breastfeeding.

If the sialyllactose or composition comprising a sialyllactose is for use in the treatment and/or prevention of reduced attention and/or impulsivity, it may be particularly effective in a subject in need of an enhancement in attention and/or a decrease in impulsivity; said subject in need an enhancement in attention and/or a decrease in impulsivity may be a subject suffering from ADHD, Alzheimers, or vascular dementia, or may be an aging human.

A nutritional composition comprising sialyllactose may be an infant formula, a starter infant formula, a follow-on formula, a preterm infant formula, a fortifier, a human milk fortifier, a baby food formula, a growing-up milk, an infant cereal composition, a food product, a medical food product for clinical nutrition, a supplement, a pet food product, or supplement for pets.

An infant formula, a starter infant formula, a follow-on formula, a preterm infant formula, a fortifier, a human milk fortifier, a baby food formula, a growing-up milk, or an infant cereal composition comprising 6'-sialyllactose may comprise said 6'-Sialyllactose (6'-SL) in an amount of from 50 mg to 5000 mg of total sialyllactose per L of the nutritional composition, for example from 60 mg to 2000 mg of total sialyllactose per L of the nutritional composition, from 80 mg to 1000 mg of total sialyllactose per L of the nutritional composition, or from 87.5 mg to 735 mg of total sialyllactose per L of the nutritional composition.

The present invention also provides a sialyllactose or a composition comprising a sialyllactose for use in the preparation of a composition for use in the prevention and/or treatment of reduced attention and/or excess impulsivity in a subject.

The present invention also provides a method of preventing and/or treating reduced attention and/or excess impulsivity in a subject, said method comprising the step of administering to said subject a sialyllactose and/or composition comprising a sialyllactose as disclosed herein, said method may optionally comprise the step of identifying a subject suffering from reduced attention and/or excess impulsivity.

DETAILED DESCRIPTION OF THE INVENTION

Figure 1:
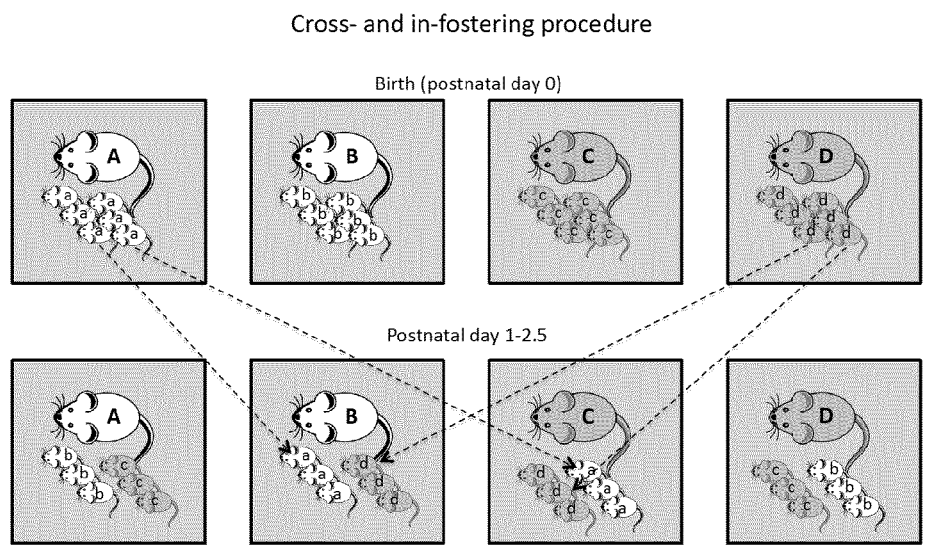
FIG. 1—Fostering scheme: starting one day after the day of birth, cross- and in-fostering procedures were performed as sketched in the lower panels.
Figure 2:
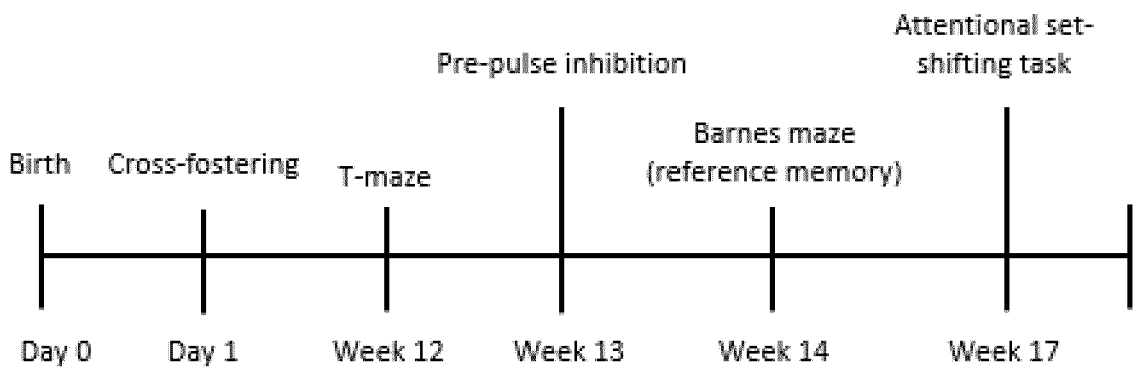
FIG. 2—Experimental timeline: The day of birth was designated as day 0.

In a first aspect of the present invention there is provided the use of a sialyllactose, or a nutritional composition comprising a sialyllactose, to enhance attention and/or to reduce impulsivity in a subject.

The term sialyllactose as used herein refers to 3'-sialyllactose (3'-SL) and 6'-sialyllactose (6'-SL). 3'-sialyllactose (3'-SL) and 6'-sialyllactose (6'-SL) are human milk oligosaccharides.

As used herein the term "3'-sialyllactose" (3'-SL, 3-SL, 3'SL, or 3SL), refers to (6R)-5-Acetamido-3,5-dideoxy-6-[(1R,2R)-1,2,3-trihydroxypropyl]-β-L-threo-hex-2-ulopyranonosyl-(2->3)-β-D-galactopyranosyl-(1->4)-D-glucopyranose (IUPAC).

As used herein the term "6'-sialyllactose" (6'-SL, 6-SL, 6'SL, or 6SL) refers to (6R)-5-Acetamido-3,5-dideoxy-6-[(1R,2R)-1,2,3-trihydroxypropyl]-β-L-threo-hex-2-ulopyranonosyl-(2->6)-β-D-galactopyranosyl-(1->4)-D-glucopyranose (IUPAC).

In an embodiment of the invention the sialyllactose is selected from the group consisting of 3'-sialyllactose (3'-SL), 6'-sialyllactose (6'-SL) and a combination of the foregoing. 6'-sialyllactose (6'-SL) may be particularly effective at enhancing attention and/or decreasing impulsivity. Accordingly, in a more specific embodiment the sialyllactose is 6'-sialyllactose (6'-SL).

3'-sialyllactose (3'-SL), and/or 6'-sialyllactose (6'-SL) may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo, Japan, or from GeneChem, Republic of Korea.

The term "impulsivity" as used herein refers to behavior characterized by little or no forethought, reflection or consideration of the consequences.

The term "attention" as used refers to the ability of a subject to focus on information or stimuli; the term may refer to any combination or specific type of attention including sustained attention, divided attention, selective attention and alternating attention.

The term "sustained attention" as used herein refers to the ability of a subject to focus on one specific task for a continuous amount of time without being distracted.

The term "selective attention" as used herein refers to the ability of a subject to select from many factors or stimuli and to focus on only one while filtering out other distractions.

The term "alternating attention" as used herein refers to the ability of a subject to switch their attention back and forth between tasks that require different cognitive demands.

The term "divided attention" as used herein refers to the ability of a subject to process two or more responses or to react to two or more different demands simultaneously e.g. to multitask.

The sialyllactose, or composition comprising a sialyllactose, may be particularly effective at enhancing sustained attention and/or divided attention. Accordingly, in an embodiment of the invention attention is a type of attention selected from the group consisting of sustained attention, divided attention, and a combination thereof. In a more specific embodiment attention is sustained attention.

The term "subject as used herein" refers to a mammal and may for example be a human or an animal such as a companion animal e.g. a cat or a dog.

In an embodiment of the invention the subject is a human or a companion animal e.g. a cat or a dog. A human may be an infant, a young child, a child, a teenager or an adult including an aging adult.

An aging adult may be a human of 50 years of age or older, for example 60 years of age or older, 70 years of age or older, 80 years of age or older, 90 years of age or older. A human infant is a human of 12 months or younger. A "young child" is a human between one and seven years of age for example between 1 and three years of age.

An infant may be a preterm infant, a small for gestational age (SGA) infant and/or an infant with a low birth weight (LBW).

The term "preterm" or "premature" means an infant or young child who was not born at term. Generally it refers to an infant or young child born prior 36 weeks of gestation.

By the expression "small for gestational age" or "SGA" it is referred to an infant or young child who is smaller in size than normal for their gestational age at birth, most commonly defined as a weight below the 10th percentile for the gestational age. In some embodiments, SGA may be associated with Intrauterine growth restriction (IUGR), which refers to a condition in which a foetus is unable to achieve its potential size.

The expression "low birth weight" is to be understood as any body weight under 2500 g at birth. It therefore encompasses:
- an infant or young child who has/had a body weight from 1800 to 2500 g at birth (usually called "low birth weight" or LBW)
- an infant or young child who has/had a body weight from 1000 to 1800 g at birth (called "very low birth weight" or VLBW)
- an infant or young child who has/had a body weight under 1000 g at birth (called "extremely low birth weight" or ELBW)

Infants or young children with low birth weight may or may not be preterm, and similarly, infants or young children who were small for gestational age may or may not be preterm.

Sialyllactose is a compound found in human breast milk (a human milk oligosaccharide), accordingly, it may be particularly beneficial if a sialyllactose, or composition comprising a sialyllactose, is administered to an infant or child, and in particular to an infant or child fed infant formula or growing up milk. Whilst breast-feeding is recommended for all infants, in some cases breast-feeding is insufficient or not possible for medical reasons. In these situations infant formula or growing up milks are a lifeline as they can be used as an alternative to mother's milk.

Accordingly, in an embodiment, the subject is a human infant or young child, and in a more specific embodiment still the subject is a human infant or child fed infant formula or growing up milk.

The subject may be a healthy subject not suffering from reduced attention and/or excess impulsivity.

Attention may be measured for example using one or more of the following tests: De Gangi Test of Attention, Wechsler Intelligence Scale for children, sustained attention tests (eye tracking) Wisconsin card sorting test (WCST), Test of Everyday Attention (TEA), Test of Variables of Attention) (T.O.V.A.®). Impulsivity may be measured for example using one or more of the following tests: Marshmallow test, Go/no-go and Stop-signal reaction time tasks, Iowa Gambling Task (IGT).

The expected performance of a healthy adult (20-29 year of age) on the WCST would be: 29 percent errors, 16 percent perseverative responses, 15 percent perseverative errors, 14 percent nonperseverative errors, 64 percent conceptual level response and 5 categories completed (data obtained from Shan et al. Adult Normative Data of the Wisconsin Card Sorting Test in Taiwan. *J Clin Med Assoc* 71(10):517-522). The expected performance of a healthy adult on the IGT is a selection of the low-risk deck is 50% of the trials.

A subject not suffering from a reduced attention would have test scores within ranges deemed non pathological for example for the type and age of the subject.

The sialyllactose or nutritional composition comprising a sialyllactose may be administered to a lactating mammal and thereby to an infant via breastfeeding. Without wishing to be bound by theory, the inventors believe that the sialyllactose or metabolites thereof may be transferred to the infant via breastmilk.

The sialyllactose or nutritional composition comprising a sialyllactose may also be administered to a pregnant mammal or a mammal trying to get pregnant (pre-pregnancy) and thereby to an infant in-utero. Without wishing to be bound by theory, the inventors believe that the sialyllactose or metabolites thereof may be transferred to the infant in-utero.

Accordingly, in another embodiment of the invention administration of the sialyllactose, or composition comprising sialyllactose, to the infant is postnatally via breastfeeding.

The composition comprising sialyllactose may be any type of composition suitable for consumption by a subject.

In an embodiment of the invention the composition is selected from the group consisting of an infant formula, a starter infant formula, a follow-on formula, a preterm infant formula, a fortifier, a human milk fortifier, a baby food formula, a growing-up milk, an infant cereal composition, a food product, a medical food product for clinical nutrition, a supplement, a pet food product, or a supplement for pets.

In a more specific embodiment of the invention the composition comprising a sialyllactose is an infant formula, a human milk fortifier, or a supplement.

A medical food product is specially formulated and intended for the dietary management of diseases or medical conditions (e.g., to prevent or treat undesirable medical conditions). A medical food product can provide clinical nutrition, for example fulfilling special nutritional needs of patients with a medical condition or other persons with specific nutritional needs. A medical food product can be in the form of a complete meal, part of a meal, as a food additive, or a powder for dissolution.

A food product, medical food or nutritional composition can be in any oral nutritional form, e.g. as a health drink, as a ready-made drink, optionally as a soft drink, including juices, milk-shake, yogurt drink, smoothie or soy-based drink, in a bar, or dispersed in foods of any sort, such as baked products, cereal bars, dairy bars, snack-foods, soups, breakfast cereals, muesli, candies, tabs, cookies, biscuits, crackers (such as a rice crackers), and dairy products.

A supplement may for example be in the form of tablets, capsules, pastilles or a liquid. The supplement can be added in a product acceptable to the consumer as an ingestible carrier or support. Non-limiting examples of such carriers or supports are a pharmaceutical, a food composition. Non-limiting examples for food compositions are milks, yogurts, curds, cheeses, fermented milks, milk-based fermented products, fermented cereal based products, milk-based powders, human milks, preterm formulas, infant formulas, oral supplements, and tube feedings.

The term "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

Generally a "starter infant formula" is intended for infants from birth as breast-milk substitute.

A "follow-up formula" or "follow-on formula" is given from the 6th month onwards. It constitutes the principal liquid element in the progressively diversified diet of this category of person.

The term "preterm infant formula" as used herein means an infant formula intended for a preterm infant.

The term "milk fortifier" as used herein refers to liquid or solid nutritional compositions suitable for mixing with breast milk (which is human milk for a human milk fortifier) or infant formula. It is used to increase the calories, protein, minerals and vitamins in breast milk fed to preterm infants or infants with a low birth weight. The term "breast milk" is to be understood as the mother's milk or the colostrum of the mother or a donor's milk or the colostrum of a donor's milk.

The term "baby food formula" as used herein means a foodstuff intended for particular nutritional use by infants or children such as young children, during the first years of life.

The term "growing-up milk" (or GUM) as used herein refers to a milk formula product given from one year onwards. It is generally a diary-based beverage adapted for the specific nutritional needs of young children.

The term "infant cereal composition" as used herein refers to a foodstuff intended for particular nutritional use by infants or children such as young children, during the first years of life.

In addition to a sialyllactose, the compositions of the invention can also comprise any other ingredients or excipients known to be employed in the type of composition in question e.g. infant formula.

Non limiting examples of such ingredients include: proteins, amino acids, carbohydrates, oligosaccharides, lipids, prebiotics or probiotics, nucleotides, nucleosides, other vitamins, minerals and other micronutrients.

If the composition is a composition for an infant or young child, the composition may for example comprise a protein source, a lipid source and a carbohydrate source. For example such a composition may comprise protein in the range of about 2 to 6 g/100 kcal, lipids in the range of about 1.5 to 3 g/100 kcal and/or carbohydrates in the range of about 1.7 to 12 g/100 kcal. If said composition is liquid, its energy density may be between 60 and 75 kcal/100 ml. If said composition is solid, its energy density may be between 60 and 75 kcal/100 g.

Non limiting examples of proteins include: casein, alpha-lactalbumin, whey, beta lactoglobulin, soy protein, rice protein, corn protein, oat protein, barley protein, wheat protein, rye protein, pea protein, egg protein, sunflower seed protein, potato protein, fish protein, meat protein, lactoferrin, serum albumin, immunoglobins, and combinations thereof.

Non limiting examples of amino acids include leucine, threonine, tyrosine, Isoleucine, arginine, alanine, histidine, isoleucine, proline, valine, cysteine, glutamine, glutamic acid, glycine, L-serine, arginine, lysine, methionine, phenylalanine, tryptophane, asparagine, aspartic acid, and combinations thereof.

Non limiting examples of carbohydrates include lactose, saccharose, maltodexirin, starch, and combinations thereof.

Non limiting examples of lipids include: palm olein, high oleic sunflower oil, high oleic safflower oil, canola oil, fish oil, coconut oil, bovine milk fat, and combinations thereof.

It may be particularly beneficial if the composition comprises fat in an amount of 25 to 30 g/100 g dry weight of the composition.

Non limiting examples of essential fatty acids include: linoleic acid (LA), α-linolenic acid (ALA). The compositions of the invention may further contain gangliosides monosialoganglioside-3 (GM3) and disialogangliosides 3 (GD3), and combinations thereof.

None limiting examples of prebiotics include: oligosaccharides optionally containing fructose, galactose, mannose; dietary fibers, in particular soluble fibers, soy fibers; inulin; and combinations thereof. Preferred prebiotics are fructo-oligosaccharides (FOS), galacto-oligosaccharides (GOS), isomalto-oligosaccharides (IMO), xylo-oligosaccharides (XOS), arabino-xylo oligosaccharides (AXOS), mannan-oligosaccharides (MOS), oligosaccharides of soy, glycosylsucrose (GS), lactosucrose (LS), lactulose (LA), palatinose-oligosaccharides (PAO), malto-oligosaccharides, gums and/or hydrolysates thereof, pectins and/or hydrolysates thereof, and combinations of the foregoing.

Further examples of oligosaccharide are described in Wrodnigg, T. M.; Stutz, A. E. (1999) Angew. Chem. Int. Ed. 38:827-828 and in WO 2012/069416 which is incorporated herein by reference.

Non limiting examples of probiotics include: *Bifidobacterium, Lactobacillus, Lactococcus, Enterococcus, Streptococcus, Kluyveromyces, Saccharoymces, Candida*, in particular selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus lactis, Lactobacillus rhamnosus, Lactobacillus johnsonii, Lactobacillus plantarum, Lactobacillus salivarius, Lactococcus lactis, Enterococcus faecium, Saccharomyces cerevisiae, Saccharomyces boulardii* or mixtures thereof, preferably selected from the group consisting of *Bifidobacterium longum* NCC3001 (ATCC BAA-999), *Bifidobacterium longum* NCC2705 (CNCM 1-2618), *Bifidobacterium longum* NCC490 (CNCM 1-2170), *Bifidobacterium lactis* NCC2818 (CNCM 1-3446), *Bifidobacterium breve* strain A, *Lactobacillus paracasei* NCC2461 (CNCM 1-2116), *Lactobacillus johnsonii* NCC533 (CNCM 1-1225), *Lactobacillus rhamnosus* GG (ATCC53103), *Lactobacillus rhamnosus* NCC4007 (CGMCC 1.3724), *Enterococcus faecium* SF 68 (NCC2768; NCIMB10415), and combinations thereof.

Non limiting examples of Nucleotides include: cytidine monophosphate (CMP), uridine monophosphate (UMP), adenosine monophosphate (AMP), guanosine monophosphate (GMP), and combinations thereof.

The composition comprising a sialyllactose, can further comprise at least one non-digestible oligosaccharide (e.g. prebiotics) in addition to the sialyllactose. Examples of such prebiotics include certain oligosaccharides, such as fructo-oligosaccharides (FOS), galactooligosaccharides (GOS), fucosylated oligosaccharides (such as 2'-fucosyllactose, 3'fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and any combination thereof), N-acetylated oligosaccharides (such as lacto-N-tetraose (LNT), N-neotetraose (LNnT) and any combination thereof). They could be usually in an amount between 0.3 and 10% by weight of composition.

Other suitable and desirable ingredients of compositions that may be employed in the composition of the invention may be described in guidelines issued by the Codex Alimentarius with respect to the type of composition in question e.g. Infant formula, HM fortifier, follow on formula, or food stuffs intended for consumption by infants e.g. infant cereals.

The composition comprising a sialyllactose, for example an infant formula, may be prepared in any suitable manner. For example, an infant formula may be prepared by blending together a protein source, a carbohydrate source, and a fat source in appropriate proportions. If used, emulsifiers may be included in the blend. A sialyllactose may be added at this point, any vitamins and any minerals may also be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger. The liquid mixture may then be cooled to about 60° C. to about 85° C.; for example by flash cooling. The liquid mixture may then be homogenised; for example in two stages at about 7 MPa to about 40 MPa in the first stage and about 2 MPa to about 14 MPa in the second stage. The homogenised mixture may then be further cooled to add any heat sensitive components; such as vitamins and minerals. The pH and solids content of the homogenised mixture is conveniently standardised at this point. The homogenised mixture is transferred to a suitable drying apparatus such as a spray drier or freeze drier and converted to powder. The powder should have a moisture content of less than about 5% by weight. If it is desired to add probiotic(s), they may be cultured according to any suitable method and prepared for addition to the infant formula by freeze-drying or spray-drying for example. Alternatively, bacterial preparations can be bought from specialist suppliers such as Christian Hansen and Morinaga already prepared in a suitable form for addition to food products such as infant formula. Such bacterial preparations may be added to the powdered infant formula by dry mixing.

The composition comprising a sialyllactose may comprise a sialyllactose in any effective amount. It is well within the purview of the skilled person to identify an effective amount based on the nature, purpose, the target subject and the dosage of the composition e.g. how many times per day the composition is to be ingested by the subject. Typically an effective amount will depend on age, size and health status of the subject, on the subject's lifestyle and on the dosage of the composition.

An effective amount may be any amount that enhances attention and/or decreases impulsivity in a subject.

Enhancements in attention and decreases in impulsivity may be measured by well-known tests as detailed hereinabove.

The enhancement of attention and/or decrease in impulsivity may only be detectable after more than 1 year, for example more than 5 years, more than 10 years, more than 20 years.

An enhancement in attention may for example be an improvement in the duration of attention i.e. how long a subject is able to focus on a task; alternatively an enhancement in attention may be an improvement in the ability of a person to pick out and focus on one piece of information from a myriad of others.

It is well within the purview of the skilled person to determine an effective dose based upon the information herein and the knowledge in the field.

For an infant formula or growing up milk, the skilled person may base the amount of a sialyllactose e.g. 3SL or 6SL on the amounts found in human breast milk produced for an infant or child of the same age, in particular by a nutritionally replete mother.

If the composition is an infant formula or growing up milk it may be particularly beneficial if the composition comprising a sialyllactose comprises sialyllactose in a concentration of 0.05 to 5 g per 100 g of the composition on a dry weight basis, e.g. from 0.1 to 2 g or from 0.2 to 1 g per 100 g of the composition on a dry weight basis.

Non limiting examples may be the composition comprises from 50 mg to 5000 mg, from 50 mg to 2500 mg of total sialyllactose per L of the nutritional composition, from 60 mg to 2000 mg of total sialyllactose per L of the nutritional composition, or from 80 mg to 1000 mg of total sialyllactose per L of the nutritional composition. In a particular embodiment, the composition comprises 2090 mg of total sialyllactose per L of composition. In another particular embodiment the composition comprises from 87.5 mg to 735 mg of total sialyllactose per L of the nutritional composition.

In an embodiment of the present invention the composition comprising sialyllactose is an infant formula, a starter infant formula, a follow-on formula, a preterm infant formula, a fortifier, a human milk fortifier, a baby food formula, a growing-up milk, or an infant cereal composition comprising 6'-Sialyllactose (6'-SL) in an amount of from 50 mg to 5000 mg per L of the nutritional composition, for example from 50 mg to 2500 mg per L of the nutritional composition, from 60 mg to 2000 mg per L of the nutritional composition, from 80 mg to 1000 mg per L of the nutritional composition and from 87.5 mg to 735 mg of per L of the nutritional composition.

In a further embodiment, a Sialyllactose may be comprised in the nutritional composition in an amount effective to provide from 110 mg to 180 mg, from 120 mg to 170 mg, or from 125 mg to 165 mg of total sialyllactose per kg body weight per day e.g. 131 mg or 162 mg of total sialyllactose per kg body weight per day.

If the composition comprising a sialyllactose comprises 3'-Sialyllactose (3'-SL) and 6'-Sialyllactose (6'-SL), it may be particularly beneficial if said 3'-Sialyllactose (3'-SL) and 6'-Sialyllactose (6'-SL) are comprised in said nutritional composition in a weight ratio between 10:1 and 1:10, such as between 10:1 and 2:1, between 8:1 and 3:1, between 6:1 and 3:1, between 5:1 and 3:1, between 5:1 and 4:1, or between 4.7:1 and 4.1:1.

As would be evident to the skilled person, the sialyllactose or composition comprising a sialyllactose as disclosed herein for use to enhance attention and/or decrease impulsivity, may also be used in the prevention and/or treatment of a reduced attention and/or excess impulsivity in a subject.

Accordingly, in another aspect of the present invention there is provided a sialyllactose and/or composition comprising a sialyllactose for use in the prevention and/or treatment of reduced attention and/or excess impulsivity.

In an embodiment the subject may be a subject suffering from reduced attention and/or excess impulsivity.

A person suffering from reduced attention and/or excess impulsivity may be a subject that does not have test scores (in standard test used to assess attention and/or impulsivity) within ranges deemed non pathological e.g. for the type and age of the subject. It is well within the purview of the person skilled in the art to determine when a subject is suffering from reduced attention and/or excess impulsivity.

Reductions in attention and excess impulsivity may be linked to a variety of cognitive conditions including Attention Deficiency Hyperactivity Disorder (ADHD), Alzheimer's disease, and vascular dementia; it is also known that attention can decline with aging. Accordingly, there may be a particular need to prevent or treat reduced attention or excess impulsivity in these patient groups.

Accordingly, in a more particular embodiment the subject is a subject suffering from ADHD, Alzheimer's disease, or vascular dementia, or is an aging adult.

In another aspect of the preset invention there is provided the use of a sialyllactose and/or composition comprising a sialyllactose as disclosed herein for use in the preparation of a composition for use in the prevention and/or treatment of reduced attention and/or excess impulsivity.

In another aspect of the present invention there is provided a method of preventing and/or treating reduced attention and/or excess impulsivity in a subject, said method comprising the step of administering to said subject a sialyllactose and/or composition comprising a sialyllactose as disclosed herein. Said method may also optionally comprise the step of identifying a subject suffering from reduced attention and/or excess impulsivity.

It should be appreciated that all features of the present invention disclosed herein can be freely combined and that variations and modifications may be made without departing from the scope of the invention as defined in the claims.

Furthermore, where known equivalents exist to specific features, such equivalents are incorporated as if specifically referred to in this specification.

As used in this disclosure and the appended claims, the singular forms "a," "an" and "the" include plural referents unless the context clearly dictates otherwise. Thus, for example, reference to "an ingredient" or "the ingredient" includes two or more ingredients. The term "and/or" used in the context of "X and/or Y" should be interpreted as "X," or "Y," or "X and Y." Where used herein, the term "example," particularly when followed by a listing of terms, is merely exemplary and illustrative, and should not be deemed to be exclusive or comprehensive.

As used herein, "about" is understood to refer to numbers in a range of numerals, for example the range of −10% to +10% of the referenced number, preferably within −5% to +5% of the referenced number, more preferably within −1% to +1% of the referenced number, most preferably within −0.1% to +0.1% of the referenced number. A range that is "between" two values includes those two values. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the total weight of the composition unless expressed otherwise. When reference is made to the pH, values correspond to pH measured at 25° C. with standard equipment.

The relative term "enhance" and "decrease" refer to the effects of a sialyllactose or a composition comprising a sialyllactose as disclosed herein on attention or impulsivity in a subject in comparison to a subject that is not administered a sialyllactose or composition comprising a sialyllactose. It is well within the purview of the skilled person to assess an improvements, increases or enhancements. The enhancement of attention and/or decrease in impulsivity may only be detectable after more than 1 year, for example more than 5 years, more than 10 years, more than 20 years.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Moreover, the description of some steps as "optional" does not imply that the other steps which are not explicitly described as optional are necessarily required.

There now follows a series of non-limiting examples that serve to illustrate the invention.

Examples

Materials and Methods
Animals and Rearing Conditions

Adult wild-type (WT) B6.129 and heterozygous (HZ) B6.129-St6gal1$^{tm2Jxm}$ breeding pairs (four males and four females and three males and four females, respectively) were purchased from a commercial breeder (The Jackson Laboratory). Upon arrival, same-sex mice were housed in same-sex groups of 2-3 in type-1 polycarbonate cages (33.0×13.0×14.0 cm) equipped with sawdust bedding, an enrichment bag (Mucedola, Settimo Milanese, Italy), metal top and ad libitum water and food pellets (Mucedola, Settimo Milanese, Italy). Mice were maintained on a reversed 12-h-light-dark cycle (light on at 7:00 PM) in an air-conditioned room (temperature 21±1° C. and relative humidity 60±10%). Two weeks after arrival, breeding triads (one male, two females) were formed. After two weeks of mating, male mice were removed and females were housed individually in standard type-1 cages. Females were checked daily for delivery and the day in which they gave birth was designated as postnatal day (PND) 0. Apart from cage cleaning once a week, dams and their offspring were kept undisturbed until weaning (on PND 25). At weaning, male and female mice were separated and located in same-sex same-litter cages; additionally, male mice were marked through ear clipping and the ear tissue removed through this procedure was used for genotyping. Homozygous knock-out (KO) and WT mice were then used for the experiments.

Fostering Procedures and Rearing

Fourteen wild type (WT) and 14 St6Gal1 Homozygous (hereafter KO) female mice have been mated with seven WT and seven KO male mice respectively. Out of this batch, 10 WT and 10 KO dams gave birth to a viable offspring. Day of birth has been designated as postnatal day (PND) 0. The fostering procedure (see FIG. 1 for details), performed between 10:00 and 13:00, required the use of four dams (two WT and two KO) at the same time. Thus, to minimise the number of subjects to be discarded due to the absence of foster dams, fostering procedures were performed between 24 and 60 hours after birth. On the day of fostering, we first removed the dams from their cage and then sexed and marked the offspring through toe tattoo ink puncture (Castelhano-Carlos, Sousa, Ohl, & Baumans, 2010). After sexing and marking procedures were completed, pups were moved to the cage housing the foster dam and covered with sawdust. Each offspring was transferred to a foster dam in order to expose all experimental subjects to the same condition. Each dam nurtured a mixed litter composed of WT and KO male and female offspring (1:1 ratio among all variables whenever possible).

At weaning (PND 25), male mice reared to the same dam were transferred together (two or three mice per cage) to standard type-1 polycarbonate cages (33.0×13.0×14.0 cm) and kept in the same conditions described above. At the end of these procedures, the experimental groups were constituted as follows:

WT offspring reared to WT dams (WT to WT), N=10
WT offspring reared to KO dams (WT to KO), N=9
KO offspring reared to WT dams (KO to WT), N=10
KO offspring reared to KO dams (KO to KO), N=10

The aforementioned subjects have then been evaluated for neurodevelopmental milestones, cognitive capabilities (inc. attention) as outlined in figure two.

Neurodevelopmental Milestones

On PND3, PND7, and PND12 mice were evaluated for the onset of neurodevelopmental milestones through the administration of Fox scales. The latter consist of a series of rapid tests to evaluate the maturity of a series of reflexes: righting (capability of mice to turn over with all four paws on the ground when placed on its back); grasping (the mouse is placed on a wire-mesh grid which is progressively tilted until the subject harmlessly falls on a soft surface, positioned 2 cm below the grid); cliff aversion (which measures the capability of mice to withdraw from a perceived visual cliff).

Furthermore, pups' bodyweight and body length were constantly monitored throughout development.

T-Maze (Week 12)

Figure 5:
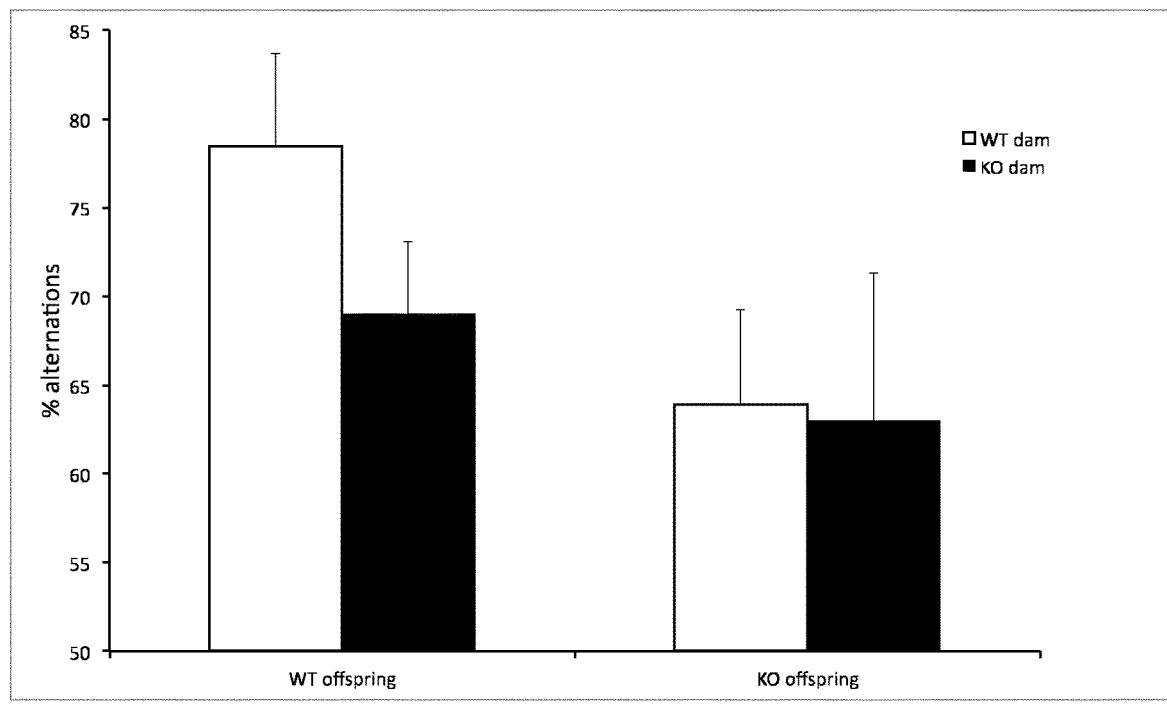

Animals were screened for perseverative behaviours in the T-maze test. The experimental apparatus consisted of an enclosed T-shaped maze, composed of three equally sized arms of (50×16 cm). Ten sessions were performed during five consecutive days (two sessions per day), always in the housing room. The experimental session, consisting of two choice trials, started with the mouse positioned in the starting compartment, facing the wall of the apparatus; then, the subject was allowed to explore the apparatus for two minutes. As soon as the animal completed the trial (entering one of the two alternative arms), such instance was scored as the first choice and the door of the arm was closed. After few seconds, the animal was gently removed from the arm, placed again in the starting compartment, and allowed to perform a second choice trial. If the subject entered the arm opposite to the previously chosen one, an instance of alternation was scored; alternatively, if the mouse re-entered the same arm, an instance of preservation was scored. The percentage of alternations, measured as the number of alternations divided by the number of completed sessions times 100, was scored for each mouse. Results are shown in FIG. 5.

Pre-Pulse Inhibition (Week 13)

Apparatus:

The apparatus (Med Associates inc. St Albans, VT, United States of America) consisted of an acoustic stimulator (ANL-925, med associates inc. St Albans, VT, United States of America) and a platform with a transducer amplifier (PHM-250-60, med associates inc. St Albans, VT, United States of America), and was positioned in a foam-lined isolation chamber (ENV-018S, Med Associates inc. St Albans, VT, United States of America), defined as startle chamber. The presence of a red light and a fan, both enclosed in the chamber, guaranteed dimmed lighting and ventilation. The platform was enclosed in a perforated compartment to ensure that the experimental subjects remained on it. Experimental data were acquired through dedicated software (SOF-815, med associates inc. St Albans, VT, United States of America).

Figure 3A:
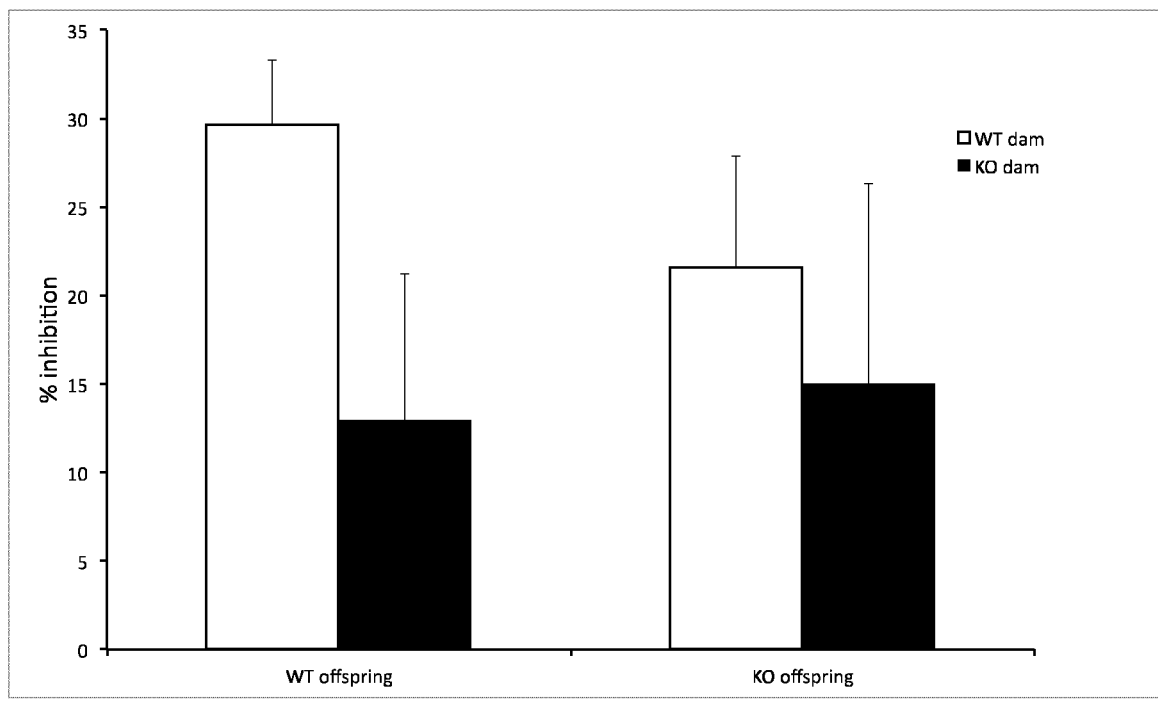
FIGS. 3a and 3b—Results of a pre-pulse inhibition test comparing WT and 6SL KO mice pups reared to either WT or 6SL KO dams.
Figure 3B:
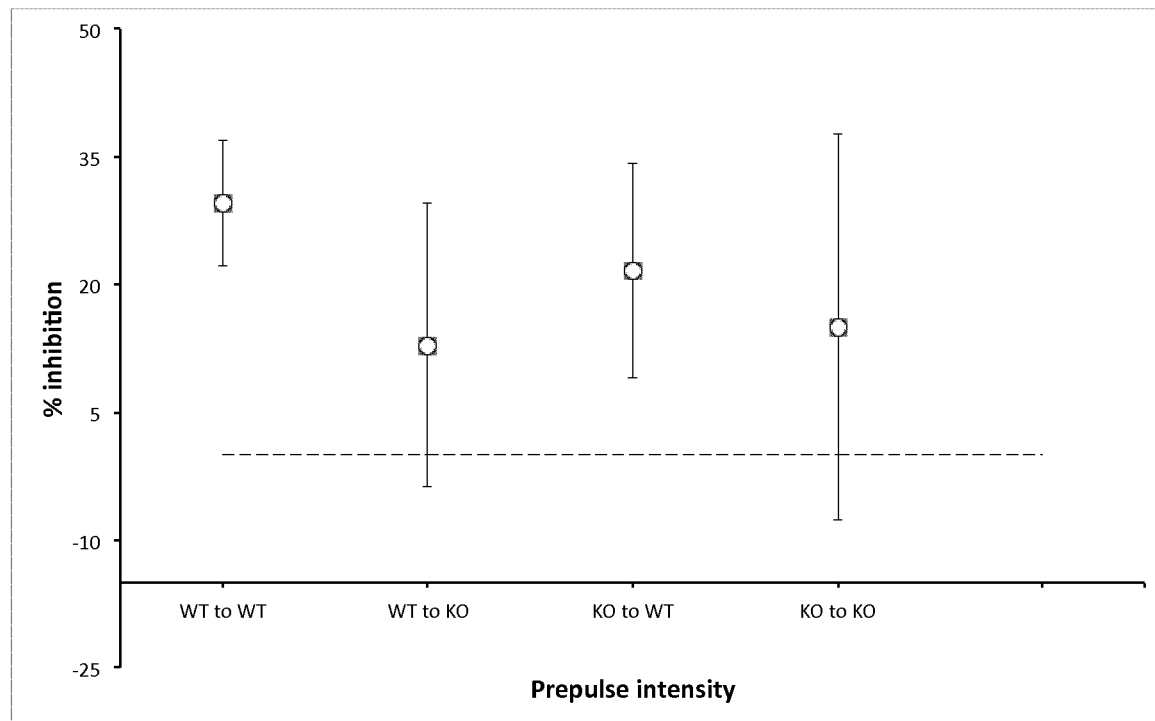

Procedure:

During habituation, each mouse was positioned individually inside the startle chamber, and left undisturbed (without any stimulus) for five minutes. On the following day, mice were placed again inside the startle chamber for testing. At the beginning of the experimental session, mice were exposed to a white noise (62 dB) for five minutes; after acclimation, mice were then exposed to a sequence of ten trials (pulses of 120 dB) interspaced by an average inter-trial interval of 15 s (block I). Then, a 16-min long session started (block II). This session entailed 56 trials comprising four different types of trial that were presented in a pseudo-randomized order. Trials were defined as follows: prepulse alone (one trial for prepulse intensity), prepulse plus pulse (four trials for prepulse intensity), startle alone (four trials) and no stimulation (four trials). The inter-trial interval varied between 10-s and 20-s to avoid habituation. Each trial started with a null period of 50 ms, followed by a prepulse noise. The intensity of the prepulse varied among four different values, represented by 67, 70, 73 or 76 dB. Following the prepulse, a startle stimulus was presented. The startle stimulus, as described previously, was constituted by a white noise 40-ms long, having the intensity of 120 dB. Prepulse and pulse stimuli were interspaced by an inter-stimulus period of 100 ms. The galvanic response was considered as the dependent variable, and was measured 65-ms following the onset of the startle. Prepulse inhibition (PPI) was measured as PPI=[(A−B)/A*100], wherein A is the Galvanic reflex registered after the startle stimulus alone, and B is the reflex registered in response to the startle in prepulse plus pulse trials. Results are shown in FIG. 3.

Barnes Maze (Weeks 14-16)

Figure 4:
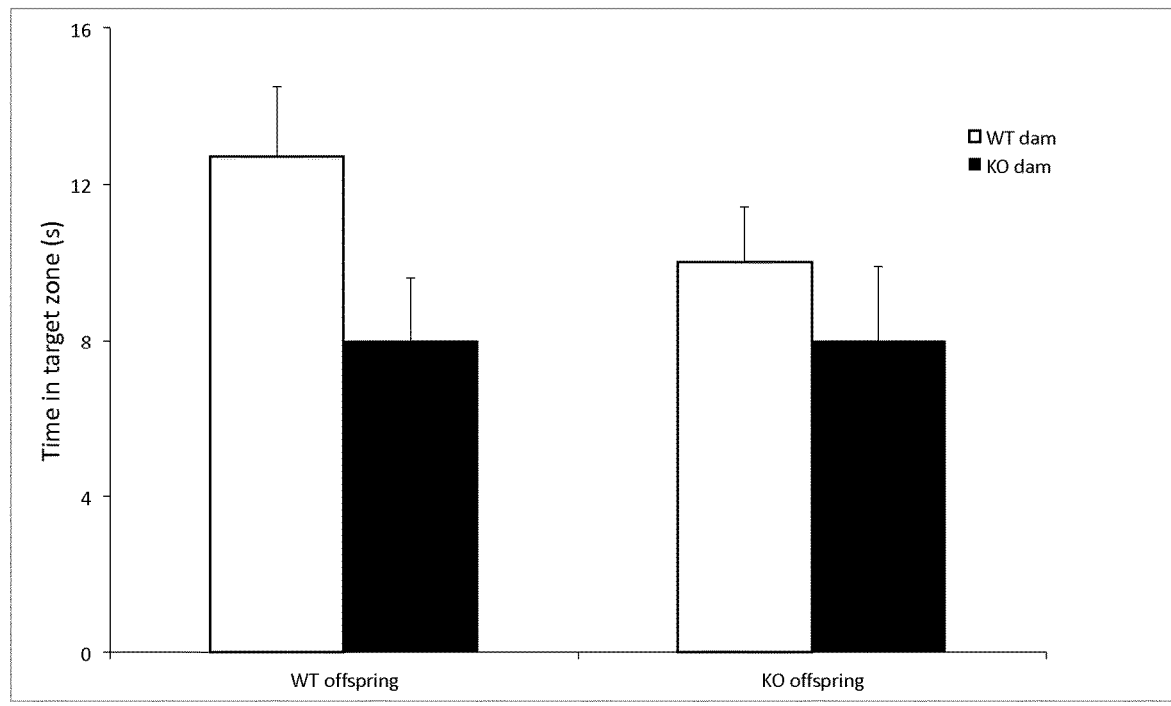
FIG. 4—Results of a Barnes Maze test comparing WT and 6SL KO mice pups reared to either WT or 6SL KO dams FIG. 5—Results of a T-maze test comparing WT and 6SL KO mice pups reared to either WT or 6SL KO dams.

In this task (Barnes, 1979), mice exposed to a bright light (85 lux) on a circular white arena are required to locate a rectangular escape box (7×37×9 cm) located underneath one of 20 holes (diameter 4 cm): the other 19 holes were covered with a black cap that provided the same visual cue offered by the target hole. The circular arena, elevated 100 cm above the floor, has a diameter of 95 cm; the 20 holes are evenly spaced on the outer surface of the arena. To avoid position bias, the position of the escape box was kept constant within individual but randomised between subjects. Before each trial, the experimental subjects were positioned inside a 25 cm high cylinder (diameter 12 cm). The experimental protocol entailed an adaptation phase, an acquisition phase and a probe test conducted 24 hours after the end of the acquisition phase. During acquisition (days 1-4), mice were daily allowed to explore the arena in two 120-sec long sessions to locate the hidden platform. If mice did not reach the target within 120 seconds, the experimenter gently located them in the escape box. Once in the target, the mouse was left there for 60 seconds before being returned to the home cage. The inter-trial interval was 10 minutes. During the acquisition phase, mice were exposed to the same testing schedule adopted for the adaptation phase, with the exception that if the mice did not reach the target they were located back in the home cage and not allowed to explore the target platform. Finally, during the probe test, mice were tested in a 90-sec long trial in which the escape box was removed and all holes were covered with the cap. Memory, during the probe test, was evaluated through the measurement of the latency to reach the target zone and time spent therein. All trials were video-recorded and analysed through a tracking software ("The Ethovision", Noldus, Wageningen, The Netherlands) providing automated information on spatial parameters (path traveled, time spent in zones, latency to reach zones). Results are shown in FIG. 4.

Attentional Set-Shifting Task (Weeks 17-23)

We adopted the attentional set-shifting task, originally developed by Birrell and Brown (Birrell & Brown, 2000) and modified by Colacicco and colleagues ((Colacicco, Welzl, Lipp, & Wurbel, 2002); see also (Macri et al., 2009)).

Apparatus:

the apparatus was an opaque PVC U-shaped box with a grid floor and a transparent plexiglass lid (45×30×15 cm). Two identical choice compartments (15×15 cm) at one end of the apparatus could be accessed through sliding doors from a starting compartment (30×30 cm). A cylindrical food cup (40 mm diameter, 35 mm high) in each choice compartment was baited with a small piece of cereal (30 mg; Honey Nut Loop, Kellogg). The food was then covered with a layer of scented digging medium (20 mm, see table). The presence or absence of food reward in a cup was indicated by either tactile (type of digging medium) or olfactory stimuli (scent of the digging medium).

Habituation:

on the day before testing, mice were given access to the apparatus for 30 min. Following this preliminary exposure mice were trained to dig into food-baited bowls during a series of 9 consecutive trials. During the first three trials mice were allowed to explore the apparatus until two food rewards, both located on the surface of the empty bowls, were retrieved. Between trials 3-6, food rewards were located on the surface of the digging media inside the bowls and mice were allowed to explore the apparatus until retrieval. Between trials 6-9, food rewards were located underneath the digging media. This procedure allowed mice to perform reliable digging.

Figure 6:
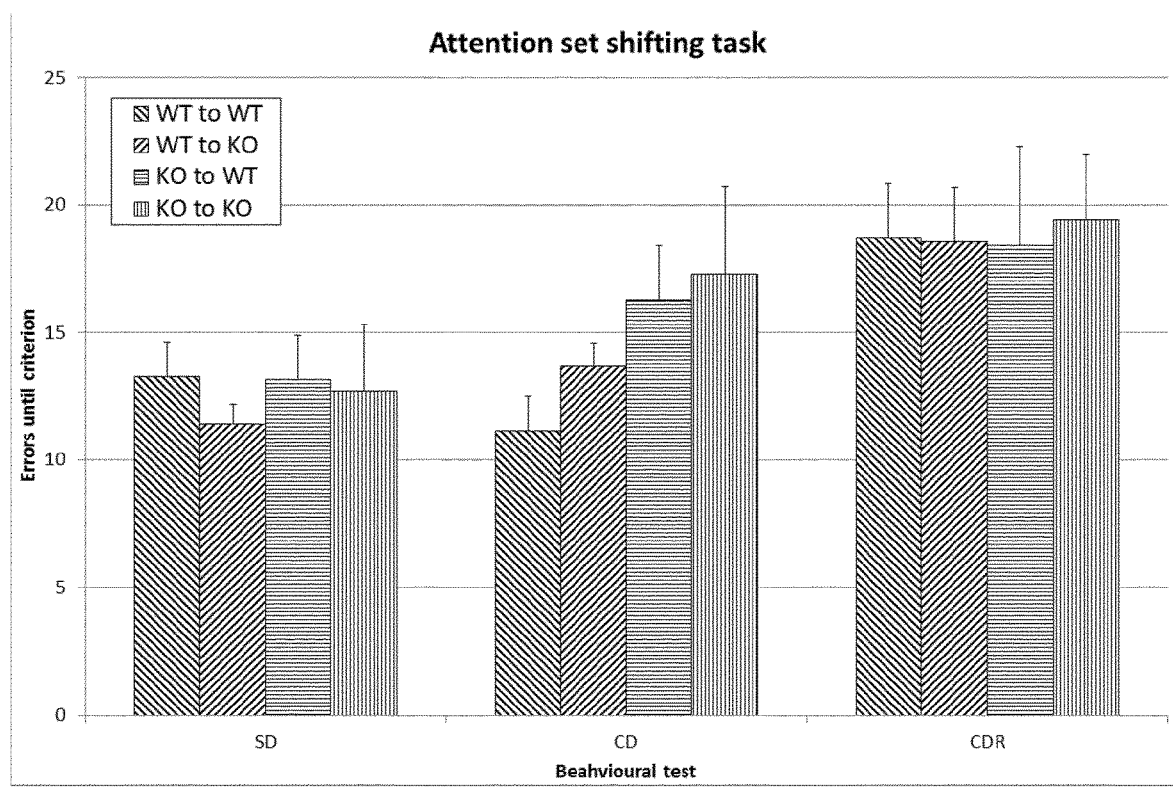
FIG. 6—Results of an attention set-shifting task comparing WT and 6SL KO mice pups reared to either WT or 6SL KO dams.

Testing:

a trial was initiated by raising the sliding wall to give the mouse access to the two digging bowls, only one of which was baited. Food-restricted mice (90% of their original body weight at the beginning of the experiment) were required to dig into a rewarded (food-baited) bowl to obtain highly palatable food pellets. Digging bowls varied across two dimensions (digging medium and scent). Digging media and odours exemplars used in this study are reported in table 1. During simple discrimination (SD) mice had to learn to discriminate between two different odours. After this stage, mice were required to perform a compound discrimination (CD), during which the baited stimulus of the previous stage was presented together with another, newly introduced, irrelevant stimulus of the other dimension (digging medium). Despite the presence of the new stimulus, the correct and incorrect exemplars remained constant (e.g. cinnamon odour was rewarded when presented in combination with either sawdust or shredded paper while thyme was not rewarded independently of the digging medium, see table 1). At the end of this stage mice had to perform CD reversal learning (CDR). For the reversal, the exemplars and the relevant dimension were unchanged: the mouse had to learn that the previously correct stimulus was now incorrect. A stage was considered complete when the mouse achieved a criterion of 8 correct trials out of 10. A session would continue until the animal ceased responding. Normally, mice would give a good profile of responses for about two hours, time after which they would just ignore the reward. Since the end of a session depended on the individual motivation to perform the task, subjects performed a variable number of trials each day. Results are shown in FIG. 6.

TABLE 1

| Stimulus exemplars used in the task | | |
| --- | --- | --- |
| Dimension | Pairing (exemplar 1) | Pairing (exemplar 2) |
| Odour | Cinnamon-Thyme | Anise-Thyme |
| Medium | Sawdust-Cotton | Sawdust-PaperChip |

Compound discriminations were based on fixed combinations of pairs of exemplars. The sequence of these combinations were presented in random combination.

The invention claimed is:

1. A method to enhance attention and/or to decrease impulsivity in a subject suffering from reduced attention or excess impulsivity, the method comprising administering a nutritional composition comprising a sialyllactose selected from the group consisting of 3'-sialyllactose (3'-SL), 6'-sialyllactose (6'-SL), and mixtures thereof to the subject, the nutritional composition does not contain galactooligosaccharide and does not contain fructooligosaccharide, wherein the attention is selected from the group consisting of sustained attention, divided attention, and combinations thereof.

2. The method according to claim 1, wherein the subject is a human infant or an aging human.

3. The method according to claim 1, wherein the nutritional composition is in a form selected from the group consisting of an infant formula, a starter infant formula, a follow-on formula, a preterm infant formula, a fortifier, a human milk fortifier, a baby food formula, a growing-up milk, an infant cereal composition, a food product, a medical food product for clinical nutrition, a supplement, a pet food product, and supplement for pets.

4. The method according to claim 1, wherein the nutritional composition is in a form selected from the group consisting of an infant formula, a starter infant formula, a follow-on formula, a preterm infant formula, a fortifier, a human milk fortifier, a baby food formula, a growing-up milk, and an infant cereal composition, the sialyllactose is 6'-sialyllactose, and the 6'-Sialyllactose (6'-SL) is comprised in the nutritional composition an amount of from 50 mg to 50000 mg of total sialyllactose per L of the nutritional composition.

5. A method for treatment of reduced attention and/or excess impulsivity in a subject suffering from reduced attention or excess impulsivity, the method comprising administering a nutritional composition comprising a sialyllactose selected from the group consisting of 3'-sialyllactose (3'-SL), 6'-sialyllactose (6'-SL), and mixtures thereof to the subject, the nutritional composition does not contain galactooligosaccharide and does not contain fructooligosaccharide, wherein the attention is selected from the group consisting of sustained attention, divided attention, and combinations thereof.

6. The method according to claim 5, wherein the subject is a human infant or an aging human.

7. The method according to claim 5, wherein the nutritional composition is in a form selected from the group consisting of an infant formula, a starter infant formula, a follow-on formula, a preterm infant formula, a fortifier, a human milk fortifier, a baby food formula, a growing-up milk, an infant cereal composition, a food product, a medical food product for clinical nutrition, a supplement, a pet food product, and supplement for pets.

8. The method according to claim 5, wherein the nutritional composition is in a form selected from the group consisting of an infant formula, a starter infant formula, a follow-on formula, a preterm infant formula, a fortifier, a human milk fortifier, a baby food formula, a growing-up milk, and an infant cereal composition, the sialyllactose is 6'-sialyllactose, and the 6'-Sialyllactose (6'-SL) is comprised in the nutritional composition an amount of from 50 mg to 50000 mg of total sialyllactose per L of the nutritional composition.

* * * * *